(12) United States Patent
Silver et al.

(10) Patent No.: US 11,974,960 B2
(45) Date of Patent: *May 7, 2024

(54) CPR CHEST COMPRESSION MONITOR WITH REFERENCE SENSOR

(71) Applicant: ZOLL Medical Corporation, Chelmsford, MA (US)

(72) Inventors: Annemarie E Silver, Bedford, MA (US); Ulrich R Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,921

(22) Filed: Oct. 31, 2018

(65) Prior Publication Data
US 2019/0099324 A1 Apr. 4, 2019

Related U.S. Application Data

(63) Continuation of application No. 15/338,747, filed on Oct. 31, 2016, now Pat. No. 10,143,621, which is a
(Continued)

(51) Int. Cl.
*A61H 31/00* (2006.01)
*A61B 5/00* (2006.01)
(Continued)

(52) U.S. Cl.
CPC ........... *A61H 31/005* (2013.01); *A61B 5/103* (2013.01); *A61B 5/1107* (2013.01);
(Continued)

(58) Field of Classification Search
CPC .... A61H 31/005; A61H 31/007; A61H 31/00; A61H 2201/0192; A61H 2201/165;
(Continued)

(56) References Cited

U.S. PATENT DOCUMENTS 443,204 A 12/1890 Davis
651,962 A 6/1900 Boghean
(Continued)

OTHER PUBLICATIONS

International Search Report and Written Opinion dated Jan. 29, 2015 from PCT Application US2014/063338.
(Continued)

*Primary Examiner* — Justine R Yu
*Assistant Examiner* — Alexander Morales
(74) *Attorney, Agent, or Firm* — ZOLL Medical Corporation (57) ABSTRACT

Methods and devices are described, such as for chest compression depth measurement for CPR performed on infants and for allowing active decompression of a patient's chest during a release phase of a chest compression cycle. An anterior segment of a resilient wrap-around structure may be positioned on the patient's sternum, including a first motion sensor. A posterior segment of the resilient wrap-around structure may be positioned on the patient's back, including a second motion sensor. Chest compressions may be provided such that the first motion sensor moves in fixed relation with the patient's sternum and the second sensor moves in fixed relation with the patient's back. Active decompression may be allowed for, including the resilient wrap-around structure exerting an expansive force on the patient's chest wall during a release phase of a chest compression cycle and hastening expansion of the patient's chest during the release phase.

31 Claims, 5 Drawing Sheets

Related U.S. Application Data continuation of application No. 14/980,901, filed on Dec. 28, 2015, now Pat. No. 9,521,977, which is a continuation of application No. 14/068,649, filed on Oct. 31, 2013, now Pat. No. 9,220,443.

(51) Int. Cl.
| | |
|---|---|
| *A61B 5/103* | (2006.01) |
| *A61B 5/11* | (2006.01) |
| *A61B 5/113* | (2006.01) |
| *A61N 1/39* | (2006.01) |
| *G01P 3/42* | (2006.01) |
| *G01P 15/02* | (2013.01) |

(52) U.S. Cl.
CPC .......... *A61B 5/1135* (2013.01); *A61B 5/4836* (2013.01); *A61B 5/4848* (2013.01); *A61B 5/486* (2013.01); *A61B 5/6823* (2013.01); *A61B 5/6835* (2013.01); *A61B 5/7405* (2013.01); *A61B 5/742* (2013.01); *A61H 31/00* (2013.01); *A61H 31/007* (2013.01); *A61N 1/3993* (2013.01); *G01P 3/42* (2013.01); *G01P 15/02* (2013.01); *A61B 5/0053* (2013.01); *A61B 2503/04* (2013.01); *A61B 2562/0219* (2013.01); *A61B 2562/0223* (2013.01); *A61H 2031/002* (2013.01); *A61H 2201/0192* (2013.01); *A61H 2201/10* (2013.01); *A61H 2201/165* (2013.01); *A61H 2201/5007* (2013.01); *A61H 2201/5043* (2013.01); *A61H 2201/5046* (2013.01); *A61H 2201/5048* (2013.01); *A61H 2201/5058* (2013.01); *A61H 2201/5079* (2013.01); *A61H 2201/5084* (2013.01); *A61H 2201/5092* (2013.01); *A61H 2230/04* (2013.01); *A61N 1/39044* (2017.08)

(58) Field of Classification Search
CPC .... A61H 2201/5043; A61H 2201/5092; A61H 2230/04; A61H 2031/002; A61H 2201/5007; A61H 2201/5048; A61H 2201/5058; A61H 2201/5079; A61H 2201/5084; A61H 2201/10; A61H 2201/5046; A61H 31/004; A61H 31/006; A61H 31/008; A61H 2031/001; A61H 2031/003; A61H 2201/0157; A61H 2201/0173; A61H 2201/1253; A61H 2201/1619; A61H 2201/50; A61H 2201/5064; A61H 2201/5066; A61H 2201/5061; A61H 2203/0043; A61H 2203/0456; A61H 2205/08; A61H 2205/084; A61H 2230/82; A61H 2230/825; A61H 2230/85; A61H 2230/855; A61H 2230/08; A61B 5/4848; A61B 5/103; A61B 5/4836; A61B 5/486; A61B 5/6823; A61B 5/6835; A61B 5/7405; A61B 5/742; A61B 5/1135; A61B 5/1107; A61B 5/0053; A61B 2562/0223; A61B 2503/04; A61B 2562/0219; A61N 1/3993; A61N 1/39044; G01P 15/02; G01P 3/42

See application file for complete search history.

(56) References Cited

U.S. PATENT DOCUMENTS

| | | | |
|---|---|---|---|
| 2,071,215 A | 2/1937 | Petersen | |
| 2,486,667 A | 11/1949 | Meister | |
| RE26,511 E | 12/1968 | Hewson | |
| 3,568,078 A | 3/1971 | Pelchat | |
| 4,355,634 A * | 10/1982 | Kanter | A61H 31/005 601/41 |
| 4,424,806 A | 1/1984 | Newman et al. | |
| 4,554,910 A | 11/1985 | Lally | |
| 4,676,232 A | 6/1987 | Olsson et al. | |
| 4,770,164 A | 9/1988 | Lach et al. | |
| 4,860,759 A | 8/1989 | Kahn et al. | |
| 4,928,674 A | 5/1990 | Halperin et al. | |
| 4,932,879 A | 6/1990 | Ingenito et al. | |
| 4,987,783 A | 1/1991 | D'Antonio et al. | |
| 4,989,611 A | 2/1991 | Zanetti et al. | |
| 5,453,081 A | 9/1995 | Hansen | |
| 5,454,779 A * | 10/1995 | Lurie | A61H 31/00 607/142 |
| 5,490,820 A | 2/1996 | Schock et al. | |
| 5,496,257 A | 3/1996 | Kelly | |
| 5,704,365 A | 1/1998 | Albrecht et al. | |
| 5,738,637 A * | 4/1998 | Kelly | A61H 31/008 601/41 |
| 5,743,864 A | 4/1998 | Baldwin, II | |
| 5,794,623 A | 8/1998 | Forbes | |
| 5,831,164 A | 11/1998 | Reddi et al. | |
| 5,844,482 A | 12/1998 | Guthrie et al. | |
| 5,876,350 A | 3/1999 | Lo et al. | |
| 5,957,856 A | 9/1999 | Weil et al. | |
| 5,978,693 A | 11/1999 | Hamilton et al. | |
| 6,013,041 A | 1/2000 | Leathers | |
| 6,027,452 A | 2/2000 | Flaherty et al. | |
| 6,090,056 A | 7/2000 | Bystrom et al. | |
| 6,174,295 B1 | 1/2001 | Cantrell et al. | |
| 6,179,793 B1 | 1/2001 | Rothman et al. | |
| 6,301,964 B1 | 10/2001 | Fyfe et al. | |
| 6,306,107 B1 | 10/2001 | Myklebust et al. | |
| 6,827,695 B2 | 12/2004 | Palazzolo et al. | |
| 6,865,413 B2 | 3/2005 | Halperin et al. | |
| 7,074,199 B2 | 7/2006 | Halperin et al. | |
| 7,108,665 B2 | 9/2006 | Halperin et al. | |
| 7,122,014 B2 | 10/2006 | Palazzolo et al. | |
| 7,220,235 B2 | 5/2007 | Geheb et al. | |
| 7,295,871 B2 | 11/2007 | Halperin et al. | |
| 7,297,125 B2 | 11/2007 | Palmer et al. | |
| 7,429,250 B2 | 9/2008 | Halperin et al. | |
| 7,775,966 B2 | 8/2010 | Stromsnes | |
| 8,002,720 B2 | 8/2011 | Hansen et al. | |
| 8,147,433 B2 | 4/2012 | Halperin et al. | |
| 8,535,251 B1 | 9/2013 | Rao | |
| 8,876,742 B2 | 11/2014 | Centen | |
| 9,101,527 B2 * | 8/2015 | Madanat | A61H 31/007 |
| 9,220,443 B2 | 12/2015 | Silver et al. | |
| 9,486,390 B2 | 11/2016 | Centen et al. | |
| 9,521,977 B2 | 12/2016 | Silver et al. | |
| 9,649,251 B2 | 5/2017 | Fossan | |
| 2003/0004445 A1 * | 1/2003 | Hall | A61H 31/00 601/41 |
| 2004/0162510 A1 * | 8/2004 | Jayne | A61H 31/005 601/41 |
| 2004/0162587 A1 * | 8/2004 | Hampton | A61N 1/39044 607/5 |
| 2005/0148909 A1 * | 7/2005 | Weil | A61H 31/006 601/44 |
| 2007/0276300 A1 * | 11/2007 | Olson | A61H 31/007 601/41 |
| 2008/0097257 A1 * | 4/2008 | Stromsnes | A61H 31/008 601/41 |
| 2008/0097534 A1 | 4/2008 | Myklebust et al. | |
| 2008/0300518 A1 * | 12/2008 | Bowes | A61H 31/007 601/41 |
| 2010/0049266 A1 * | 2/2010 | Ochs | A61H 31/005 607/5 |
| 2010/0198118 A1 | 8/2010 | Inati | |
| 2010/0211127 A1 * | 8/2010 | Eerden | A61H 31/005 607/5 |
| 2010/0228165 A1 * | 9/2010 | Centen | A61H 31/00 601/41 |
| 2011/0201979 A1 * | 8/2011 | Voss | A61H 31/005 601/41 |

(56) References Cited

U.S. PATENT DOCUMENTS

| | | | | |
|---|---|---|---|---|
| 2012/0010543 | A1* | 1/2012 | Johnson | A61H 31/005 601/41 |
| 2012/0016179 | A1* | 1/2012 | Paradis | A61H 31/005 600/17 |
| 2012/0083720 | A1* | 4/2012 | Centen | A61H 31/007 601/41 |
| 2012/0184882 | A1 | 7/2012 | Totman et al. | |
| 2012/0191014 | A1* | 7/2012 | Fossan | A61H 31/004 600/587 |
| 2012/0226204 | A1* | 9/2012 | Coleman | A61N 1/37247 601/41 |
| 2012/0330200 | A1* | 12/2012 | Voss | A61H 31/004 601/41 |
| 2013/0072830 | A1* | 3/2013 | Illindala | A61H 31/006 601/41 |
| 2013/0184618 | A1* | 7/2013 | Woerlee | A61H 31/004 601/41 |
| 2013/0225972 | A1 | 8/2013 | Banville et al. | |
| 2014/0005578 | A1* | 1/2014 | Woerlee | A61H 31/004 601/41 |
| 2014/0060546 | A1* | 3/2014 | Pino | A61B 5/4836 128/845 |
| 2014/0107541 | A1* | 4/2014 | Sullivan | A61N 1/3925 601/41 |
| 2014/0155792 | A1* | 6/2014 | Karve | A61H 9/0078 601/41 |
| 2014/0171840 | A1 | 6/2014 | Aelen et al. | |

OTHER PUBLICATIONS

Pinchak, et al., Accelerometer Measurements in CPR, 37th ACEMB 32 (1984).

Pinchak, et al., Chest Wall Acceleration and Force Measurements in Simulated Manual and Mechanical Cardiopulmonary Resuscitation, 16 Critical Care Medicine 151 (1988).

Strohmenger, et al., Spectral Analysis of Ventricular Fibrillation and Closes-Chest Cardiopulmonary Resuscitation, 33 Resuscitation 155 (1996).

Supplementary European Search Report for EP Application No. 14859263.7, dated Jun. 13, 2007, 8 pages.

* cited by examiner

CPR CHEST COMPRESSION MONITOR WITH REFERENCE SENSOR

FIELD OF THE INVENTIONS

The inventions described below relate the field of CPR.

BACKGROUND OF THE INVENTIONS

Chest compressions provided as a component of cardio-pulmonary resuscitation (CPR) should be accomplished at a consistent depth of about 2 inches, according to the CPR Guidelines 2010. This is difficult to accomplish, especially over a long course of CPR. Chest compression monitors, such as those used in ZOLL Medical Corporation's CPR D Padz® and Real CPR chest compression monitor, give real time feedback to a CPR provider, measuring the depth and rate of compressions achieved during CPR and providing immediate reports of achieved chest compression depth to the CPR provider. This helps the CPR provider achieve the desired compression depth and also helps the CPR provider realize when he is too fatigued to provider proper chest compressions. In use, the chest compression monitor is sandwiched between the chest of a cardiac arrest victim and the hands of a CPR provider during compressions. These chest compression monitors are free-floating, and can accurately measure chest compression depth without reference to any external reference or input. This is described in Halperin, et al., CPR Chest Compression Monitor, U.S. Pat. No. 6,390,996 (May 21, 2002), as well as Palazzolo, et al., Method of Determining Depth of Chest Compressions During CPR, U.S. Pat. No. 7,122,014 (Oct. 17, 2006). Nonetheless, these chest compression monitors can be augmented with reference sensors, to ensure or improve accuracy when chest compressions are performed on a patient that is coincidentally subject to gross vertical movements. For example, Palazzolo, et al., Method Of Determining Depth Of Chest Compressions During CPR, U.S. Pat. No. 7,122,014 (Oct. 17, 2006) disclosed a system including a chest compression monitor disposed on the chest of a cardiac arrest victim and a reference sensor disposed elsewhere on the body of the cardiac arrest victim or a gurney supporting the cardiac arrest victim.

For adults, CPR chest compressions are delivered while the patient is supine, supported by a sufficiently rigid surface (a floor, gurney, or hospital bed). For infants, CRP chest compressions are provided with one of two methods. The preferred method is the two-thumb method, and entails grasping the infants thorax with both hands, placing both thumbs over the sternum (with the fingers supporting the back of the infant) and compressing the sternum with the thumbs. Another method, suggested for use by a lone rescuer, is referred to as the two-finger method, and entails compression of the infant's chest with two fingers placed over the inter-mammary line (superior to the xiphoid process). Compressions should be about 1.5 inches (3.8 cm) (one third of the thickness of the thorax of 4.5 inches (11.4 cm), which is rough estimate of infant chest thickness which is of course variable depending on the age of the infant patient). The chest should be released completely after each compression. According to the American Heart Association, the 2-thumb-encircling hands technique is preferred over the 2-finger technique because it produces higher coronary artery perfusion pressure, results more consistently in appropriate depth or force of compressions, and may generate higher systolic and diastolic pressures.

In another aspect of CPR, active compression-decompression CPR has been suggested as an adjunct to CPR.

Active compression-decompression refers to compression techniques which include some mechanism for actively lifting the chest wall between compression down strokes, rather than merely relying on the natural resilience of the chest wall to expand the chest between compressions. Active decompression devices, such as proposed by Steen, Systems and Procedures for Treating Cardiac Arrest, U.S. Pat. No. 7,226,427 (Jun. 5, 2007), use a piston to compress the chest. The piston is driven up and down by a motor. A suction cup on the lower face of the piston is intended to pull the chest wall up with the piston. Active decompression is not yet recommended for pediatric use.

SUMMARY

The devices and methods described below provide for chest compression monitoring during CPR provided to infant cardiac arrest victims, especially where compressions are provided with the two-thumb method. The device includes a chest compression monitor and a reference sensor mounted on the tips of an easily deformable open frame which fits around the infant's thorax. The open frame is place around the infant's thorax, with one sensor disposed on the compression point and one sensor disposed on the infant's back, and the CPR provider performs the two-thumb compression technique with one sensor trapped between his thumbs and the infant's chest, and the other sensor trapped between the rescuer's fingers and the infant's back. The device used to measure chest compression depth can be augmented to provide active decompression for infant cardiac arrest victims. The frame which holds the device may be resilient, such that it forcefully returns to an open position, and the tips of the frame may be adhesive, such that they adhere to the infants chest and back, such that upon each release by the CPR provider, the frame exerts a gently expansive force on the infant's thorax.

DETAILED DESCRIPTION OF THE INVENTIONS

Figure 1:
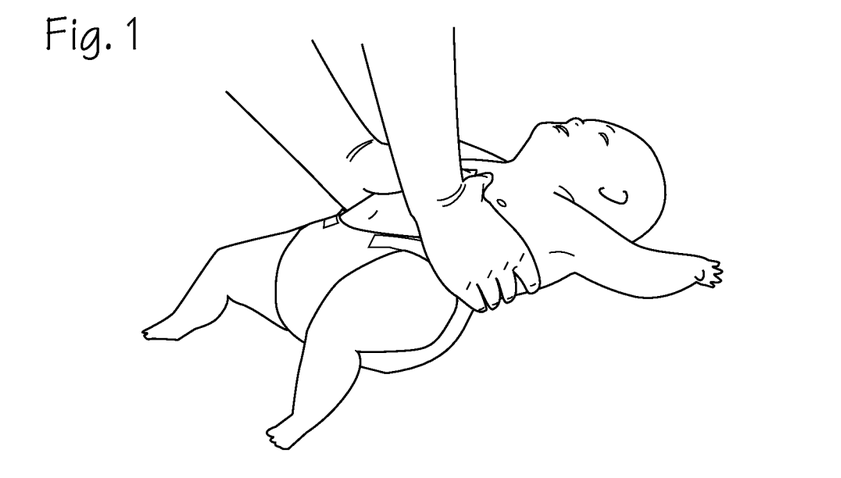
FIG. 1 illustrates the two-thumb technique for accomplishing CPR compressions on an infant.

FIG. 1 illustrates the two-thumb technique for accomplishing CPR compressions on an infant. The infant is shown supine, supported on a surface. A CPR provider has placed his hands around the infant's thorax, placing his thumbs over the infant's sternum with his fingers wrapping over the axillary area under the infant's arms and around the infant's back. In this method, the CPR provider squeezes the infant's thorax, with the thumbs pressing on the sternum, to push the sternum toward the spine. These compression should be accomplished at a rate of 100 compressions per minute and a depth of 1.5 inches (3.8 cm)(or about one-third of the total thickness of the thorax).

Figure 2:
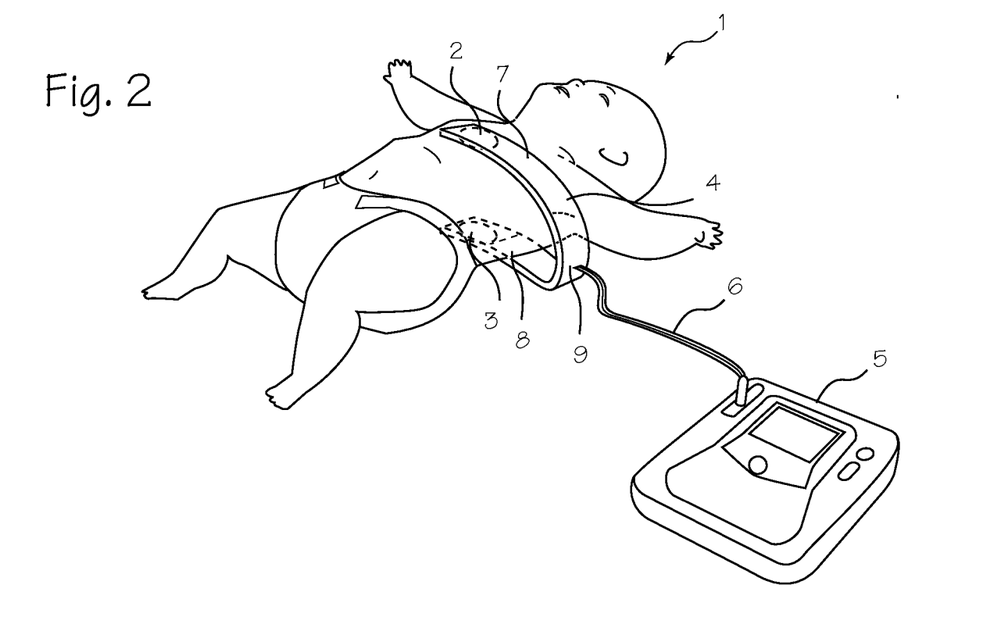
FIG. 2 illustrates placement of the new chest compression depth monitoring system on an infant cardiac arrest victim.

FIG. 2 illustrates placement of the new chest compression depth monitoring system on an infant cardiac arrest victim 1. The system includes a first sensor 2 located over the sternum and a second sensor 3 located on the back. These two sensors are mounted on a frame 4, which, as illustrated, is a U-shaped frame defining an open space which accommodate the infant. The sensors are mounted on the frame such that, with the frame disposed about the infant's thorax, the sensors may be properly located over the sternum and opposite the sternum on the infant's back. The sensors are operably connected to an automatic external defibrillator (AED) 5 through cable 6. The AED box 5 includes a control system, a display and speaker, and a defibrillator. The display and speaker are operable for providing visual or audio feedback to the CPR provider regarding the depth and rate of the compressions provided by the CPR provider, and comprise means for providing feedback to the CPR provider. The AED also includes an input device, such as a keyboard, soft-keys or touchscreen (which may also be used as the display). The control system (a computer) is programmed to interpret the acceleration signals to calculate compression depth and/or velocity (specifically, release velocity), and generate visual displays and/or audio prompts to be displayed or played to guide the CPR provider. (The control system also analyzes ECG signals obtained from ECG electrodes, not shown, to determine if defibrillating shock should be applied, and may prompt the user to apply shock or automatically operate the defibrillator to apply shock to the infant patient.) The control system can also be provided in a stand-alone device, without the defibrillator function. The control system comprises at least one processor and at least one memory including program code with the memory and computer program code configured with the processor to cause the system to perform the functions described throughout this specification.

Figure 3:
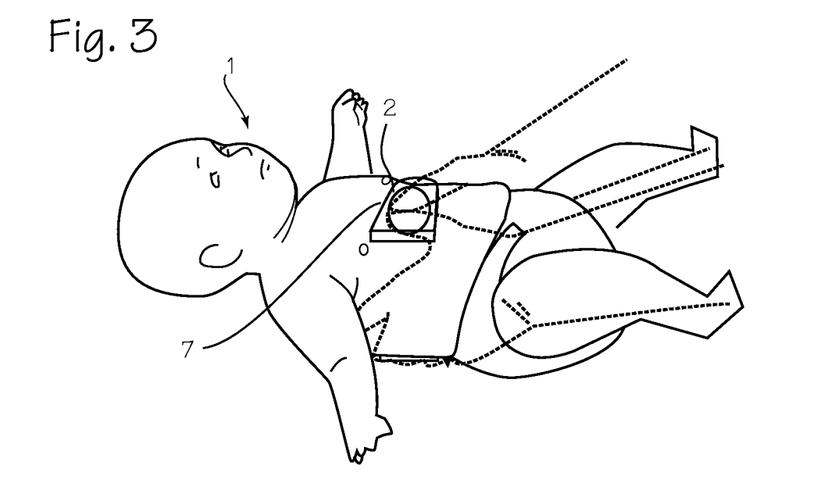
FIG. 3 illustrates the two-thumb technique for accomplishing CPR compressions on an infant while the system of FIG. 2 is installed on the infant.

FIG. 3 illustrates the two-thumb technique for accomplishing CPR compressions on an infant while the system of FIG. 2 is installed on the infant. As in FIG. 2, the frame 4 is disposed about the thorax of the infant, with the first sensor 2 disposed over the sternum of the infant and the second sensor 3 (see FIG. 2) disposed on or under the back of the infant. The rescuer is shown with his/her thumbs over the first sensor, trapping the first sensor between the rescuer's thumbs and the infant's sternum, and the fingers of both hands wrapped around the infant's thorax, preferably trapping the second sensor between the fingers of the rescuer and the back of the infant.

Figure 4:
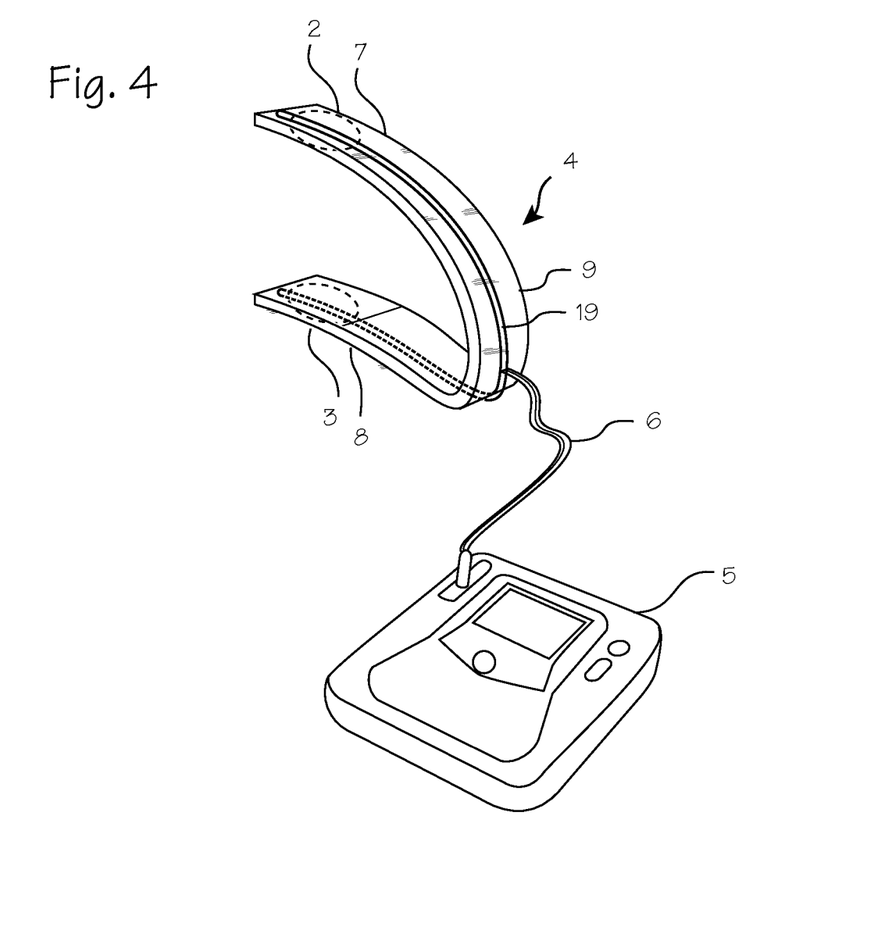
FIG. 4 illustrates the frame in isolation.

FIG. 4 illustrates the frame in isolation. The frame may take on many forms, and is illustrated as a U-shaped frame 4, comprising two laterally extending elements 7 and 8 joined by an arcuate segment 9. The sensors 2 and 3 are mounted near the tips 10 and 11 of extending elements, so that they can easily be located with the first sensor 2 disposed over the sternum of the infant and the second sensor 3 disposed on or under the back of the infant. The frame construction assures proper placement of the sensors on the anterior and posterior surface of the infant, so that motion signals from each sensor can be used to measure the chest wall motion induced by the CPR compressions accomplished by the CPR provider, taking into account any anterior/superior motions of the infants entire thorax attendant to the two-thumbs technique. The frame is preferably resilient and biased to an open configuration (as large or larger than the thickness of the infant's chest), such that after each compression, it resiliently returns to an open position, but may instead be merely flexible such that upon release of the chest by the CPR provider the frame expands due to the natural resilience of the infant's chest. The frame is illustrated as an open U-shaped frame, but may be most any shape useful to properly locate the sensors above and below the infant's thorax and convenient to dispose about the infant's thorax. So, for example, the frame may be an oval which completely encircles the thorax. The frame may be provided in various sizes, with each size chosen to suit a range of infants and small children of various sizes, or it may be provided in single size suitable for a wide range of patient sizes.

If the system is intended to impart some expansive force on the chest between compression down strokes, during the release phase or upstroke of a compression, the inner surfaces of the extending segments of a resilient frame, which inner surfaces may include the inner surfaces of the sensor assemblies (or housings, if they are discrete from the extending segments), may be covered or coated with an adhesive layer suitable for adhering the extending segments to the thorax of the infants. The adhesive may be limited to the tips of the extending segments, such that only the tips of the extending segments adhere to the chest wall. With this construction, with each release of compression force, the resilient expansion of the frame with exert expansive force on the chest wall, and provide a degree of active decompression between each compression.

Figure 5A:
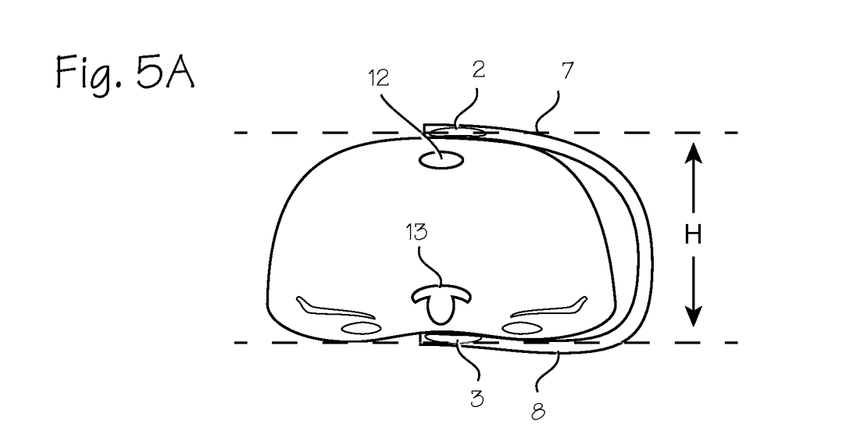
FIGS. 5A, B and C illustrate the compression frame during compressions of the infants thorax.
Figure 5B:
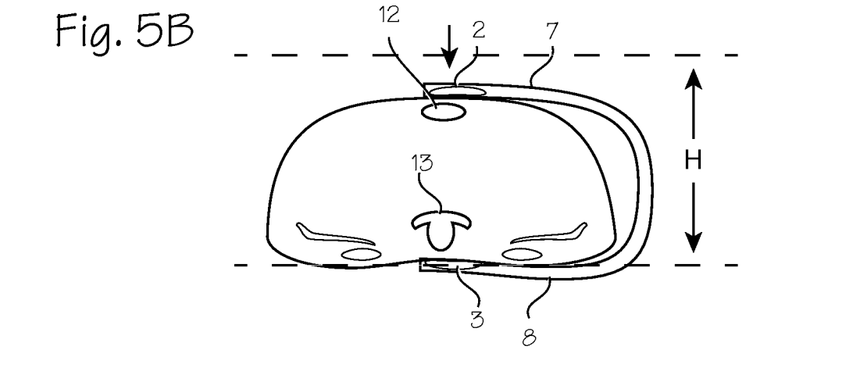
Figure 5C:
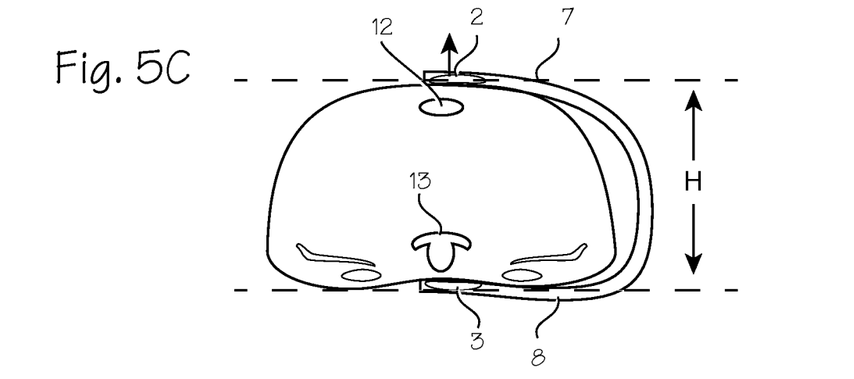

FIGS. 5A, B and C are cross sections of the frame, illustrating the action of the frame on the thorax of the infant. As shown in FIG. 5A, the frame is slipped over the infant's chest, such that the anterior sensor 2 is disposed directly over the sternum 12, and the posterior sensor 3 is located under the spine 13. The CPR provider squeezes the infants chest, using the two-thumbs technique, to achieve the compressed state illustrated in FIG. 5B. FIG. 5B represents the compression stroke or compression phase of the compression cycle. Upon release, the infants chest will expand, as shown in FIG. 5C, to its original thickness. Where the interior surfaces of the extending segments are adhesive, the resilient expansion of the frame lead to an expansive force applied to the chest, which hastens the expansion of the chest during the release phase of the compression cycle.

Figure 6:
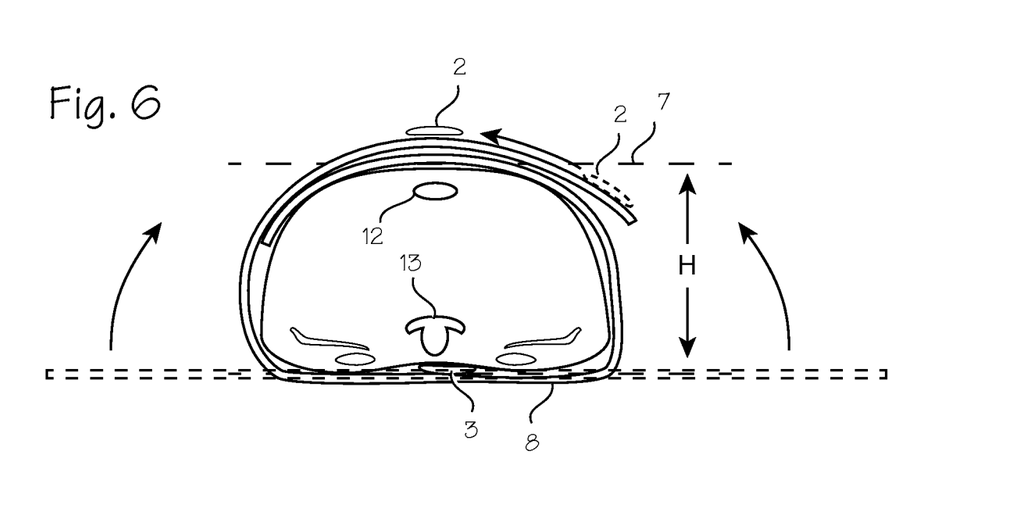
FIG. 6 illustrates a wrap-around frame which can be fitted on an infant cardiac arrest victim.

FIG. 6 illustrates a version of the frame which wraps entirely around the infant cardiac arrest victim. In FIG. 6, the frame 4 may be provided in a length exceeding the circumference of the infant, and sufficient to entirely surround the infant's thorax (practically, the wrap around frame will be provided in a single length long enough to surround infants of various sizes). As with the frames of the earlier figures, the frame of FIG. 6 is resiliently biased to open to a circumference larger than the circumference of the infant. The frame may have an initial configuration which is substantially flat, in which case it is folded up and around the infant's thorax as shown, and adjusted to obtain a close fit with the infant's thorax before compressions are initiated. The frame may instead have an initial configuration which is substantially circular, in which case it is spread open to accommodate the infant's thorax and adjusted to obtain a close fit with the infant's thorax before compressions are initiated. The anterior sensor 2 may be releasably fixed to the frame, with hook and loop fastener or other fastener, so that it can be relocated to the infant's sternum when the frame is adjusted to fit about the infant.

Figure 7:
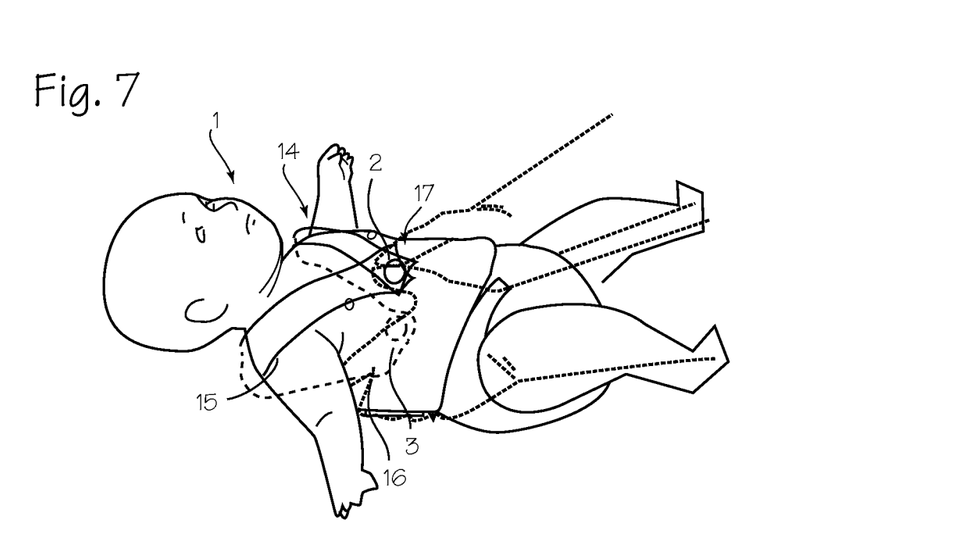
FIG. 7 illustrates a variation of the frame, applied to infant cardiac arrest victim over the shoulders of the infant.

FIG. 7 illustrates a variation of the frame, applied to infant cardiac arrest victim over the shoulders of the infant. The frame of FIGS. 2 through 4 can of course be fitted over one shoulder of the infant, at the option of the CPR provider. The frame 14 of FIG. 7 comprises a front portion 15 and back portion 16, with an opening between the two to accommodate the infant's head. From the side or lateral aspect, the frame is U-shaped. As with the frame of FIGS. 2 through 4, this frame may be resilient and biased to an open position, with the distance between the sensors in the open, relaxed configuration being slightly greater than the anterior-posterior thickness of the infant's thorax. The sensors 2 and 3 are mounted on the frame, with the anterior sensor 2 mounted on the front portion and the posterior sensor 3 mounted on the back portion. As illustrated, viewed from the front or anterior aspect, the front portion is V-shaped, with the vertex 17 of the V, where the anterior sensor 2 is located, disposed over the sternum of the infant. The posterior sensor 3 located directly below the anterior sensor, on the back portion and located at the back of the infant. The vertex of the V serves as an easily recognizable landmark for the user when applying the frame to the infant, but the frame may be made in other configurations that permit the frame to be slipped over the infant's head (for example, a bib or pinafore), and provide for locating the anterior sensor over the infant's sternum.

Figure 8:
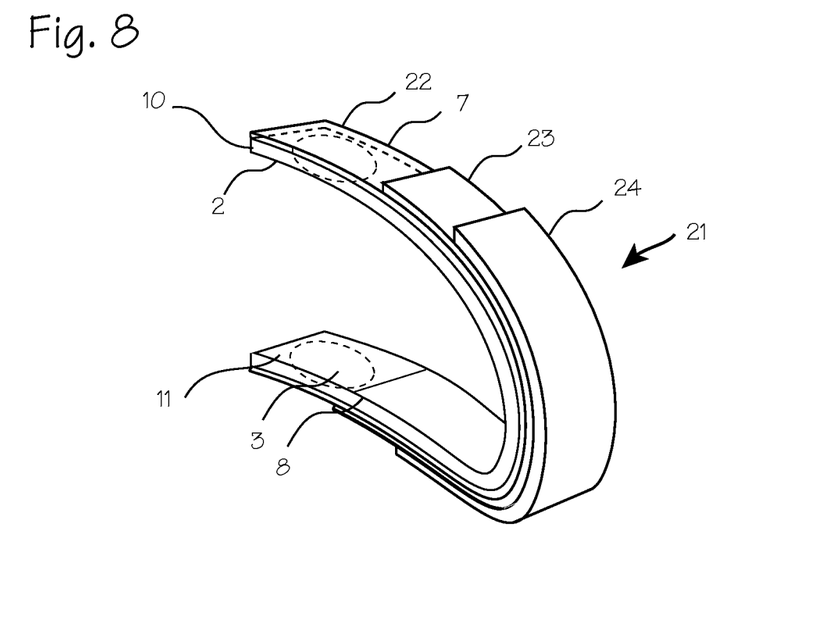
FIG. 8 illustrates a frame for use in the system which can be easily modified to adjust the resilience of the frame.
Figure 9:
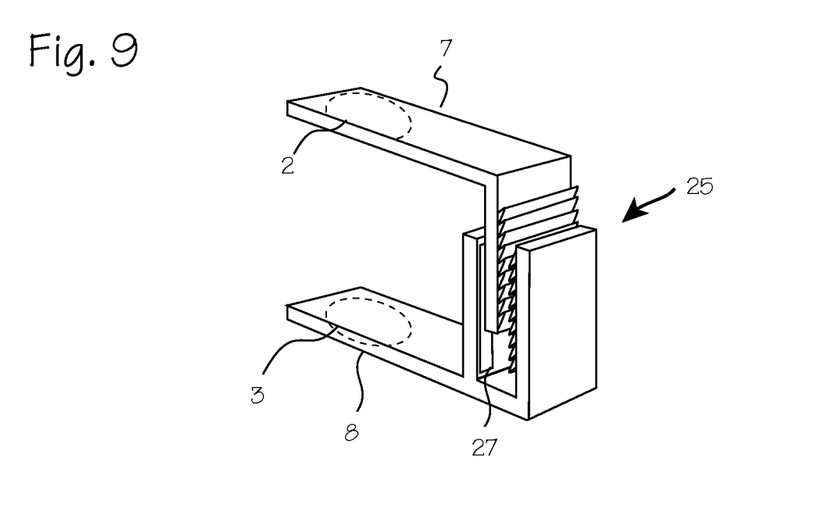
FIG. 9 illustrates a frame for use in the system, which can be adjusted to fit infants of various sizes.

The frame can be provided in a single size chosen to fit most infants subject to the two-thumb technique, and configured with a resilience and expansive force suitable for applying active compression/decompression for most infants, or the frame can provided in a variety of sizes, leaving to a CPR provider to select an appropriate size and/or resilience at the point of use, or adjust size and/or resilience of the frame at the point of use when the size of the actual patient is known. Should it be desirable to adjust these properties, the frame can be modified as illustrated in FIGS. 8 and 9. FIG. 8 illustrates a frame for use in the system which can be easily modified to adjust the resilience of the frame. The frame 21 holds the anterior and posterior sensors 2 and 3 at the tips of anterior and posterior extending elements 7 and 8. The frame 21 is resilient, and manufactured to exert a first level of expansive force when released from compression. The frame comprises one or more additional layers 22, 23 and 24, which are also resilient. The additional layers are secured to the underlying layers with adhesive or a mechanical interlock, such that they are releasable secured to underlying layers and may be removed easily by the CPR provider. To adjust the resilience of the frame, one or more releasable layers may be removed, thus weakening the frame and reducing its resilience.

FIG. 9 illustrates a frame for use in the system, which can be adjusted to fit infants of various sizes. The laterally extending segments 7 and 8 are connected to each other through an expandable ratcheting mechanism 25. The ratcheting assembly may be used to expand or collapse the laterally extending segments 7 and 8 to size the device to a particular infant cardiac arrest victim. As with the U-shaped frames illustrated above, the sensors 2 and 3 are disposed within or on the tips of the extending segments.

The sensors may include any sensor technology suitable for determining compression depth. Accelerometers may be used, as described in Halperin, U.S. Pat. No. 6,390,996 and Palazzolo, U.S. Pat. No. 7,122,014. In this case, the anterior sensor may be an accelerometer-based chest compression monitor as described in Halperin and Palazzolo, and the posterior sensor can be a reference accelerometer or another accelerometer-based chest compression monitor. The accelerometers are capable of producing acceleration signals corresponding to the acceleration of the chest and the acceleration of the back, and the control system is operable to integrate the acceleration signal received from the accelerometers, integrating and combining those signals to determine the depth of chest compression and produce a measured depth signal. The control system is also programmed to report the measured depth to the CPR provider through the display or audio output, or compare the measured depth signal to a desire depth of compression and report to the CPR provider whether the achieved depth of compression meets or fails to meet the desired depth. Velocity sensors may also be used, in which case the control system is programmed to process the velocity signal received from the velocity signals to achieve the same ends. Also, the control system may be programmed to process the acceleration signals to determine the compression velocity, release velocity, and compression rate to produce corresponding signals, and provide reports and feedback to the CPR provider regarding these parameters.

Magnetic motion sensors, such as those which use an electromagnetic source and sensor, described in Geheb, et al., Method and Apparatus for Enhancement of Compressions During CPR, U.S. Pat. No. 7,220,235 (May 22, 2007) and Centen, et al., Reference Sensor For CPR Feedback Device, U.S. Pub. 2012/0083720 (Apr. 5, 2012), may also be used to determine compression depth. In this case, the one sensor is a magnetic field sensor, and the other sensor is replaced by a magnetic field generator (a permanent magnet or an electromagnet), and the control system is operable to receive and process distance information from the electromagnetic sensor to determine compression depth, release velocity, and compression rate. These and any other means for determining compression depth, compression rate, and release velocity may be used.

The control system is programmed to receive signals corresponding to motion of the chest wall and motion of the thorax (motion of the back, as sensed by the sensor 3, and determine the depth of compression achieved during CPR based on those signals. (In the magnetic sensing embodiment, the control system is programmed to determine the depth of compression achieved during CPR based signals from the magnetic field sensor.) The control system is programmed to generate a signal corresponding to the determined chest compression depth which may be used to provide a display indicating achieved chest compression, or may be used by other equipment. The control system is further programmed to compare the determined depth of compression with predetermined desired chest compression goals, and provide feedback to a CPR provider regarding the adequacy of chest compression depth, including whether achieved chest compression depth is inadequate, adequate, or excessive as compared to the predetermined goals. The feedback can include audio or visual prompts to compress more deeply, prompts to compress at a faster or slower rate, and prompts to quickly and completely release the chest of the patient after each compression. The feedback can also include haptic feedback, provided when compression depth is adequate, inadequate, or excessive, through vibrators disposed on the frame.

The system can be adapted to determine an initial measurement of the patients chest. The sensors mentioned above may be used, or additional sensors may be added to the frame, to measure the patient's chest prior to the start of chest compressions. This information can be use to advise a CPR provider to limit expansive motion of the frame during release (to limit the active decompression)(limiting the expansive motion of the frame during release can be accomplished merely by holding the frame between compressions, and not allowing it to fully expand), and to advise the CPR provider regarding the adequacy of chest compressions based on the size of the patient. The distance between the sensors 2 and 3 can be determined, using signals from the sensors, where applicable. For example, where the sensors are a magnetic field sensor and a magnetic field generator, the position of the magnetic sensor in the magnetic field generated by the magnetic field generator can be determined.

Additional sensors may be used to size the patient. Distance sensors and proximity sensors at the tips of the frame, near sensor 2, for example, can determine the distance from the frame tip to the patient, and thereby calculate the size of the patient. This system may require operator input, to inform the system when the frame is disposed about the patient such that the bottom frame tip and sensor 3 are in place below the patient, so that the control system can then calculate the patient chest height based on the known distance between the frame tips and the measured distance between the upper frame tip and the chest wall of the patient. In another system, strain sensors disposed on or within the frame can be used to determine the shape of the frame, and thus the distance between the frame tips. For example, a shape monitoring cable (item 19 in FIG. 4) comprising linear arrays of fiber Bragg gratings may be disposed on or within the frame, and a control system may operate a light source and light sensors to determine the shape of the frame. This system may require operator input, to inform the system when the frame is disposed about the patient such that the bottom frame tips and sensor 2 and sensor 3 are in contact with the patient, so that the control system can then calculate the patient chest height based shape of the frame as determined by the shape monitoring cable. Shape monitoring cables suitable for use in this embodiment may also include piezo-electric strain gauges and other forms of strain gauges.

For the frame of FIG. 9, an optical, magnetic or capacitive encoder or other position sensor 27 can be used to determine the position of ratcheting segments relative to each other, and from this information the control system can determine the distance between the tips and the chest height of the patient. Again, with operator input informing the system when the frame is disposed about the patient such that the bottom frame tips and sensor 2 and sensor 3 are in contact with the patient, the control system can then calculate the patient chest height based on the encoder reading. Thus, for the initial determination of the size of the patient, sensors mounted on the frame tips, encoders disposed on an adjustable portion of the frame, a shape monitoring cable disposed on the frame, and any other suitable means of determining the distance between the frame tips can be used, in conjunction with input from the CPR provider indicating that the frame tips are in close proximity to the patient/s thorax.

In each case, the initial measurement of the size of the patient's thorax can be use by the control system to select advisory parameters, such as the amount of compression desired, and the amount of active decompression desired, for the patient based on patient size, and generate advisory prompts to the CPR provider based on patient size. The compression depth targets for infants should be about ⅓ of the infant's chest height, and the appropriate chest compression goals can be selected by the control system programmed to calculate the chest compression goals based on the measured size of the patient. Thus, for CPR compressions performed on small children, the control system would be programmed to provide a positive advisory (that compression are adequate) or a negative advisory (that compression are excessive, or active decompression too expansive) for small compressions and active decompressions, and also programmed to provide a positive advisory (that compression are adequate) or a negative advisory (that compression are excessive, or active decompression too expansive) for slightly larger compressions and active decompressions for CPR performed on a larger child.

In use, a CPR provider will place the frame around the thorax of an infant cardiac arrest victim, with one sensor on the victim's chest, over the victim's sternum, and the second sensor under the infant's spine. The CPR provider will then grasp the infant's thorax with both hands, placing his thumbs over the infant's sternum and extending his fingers around the thorax, in the two-thumbs position. The CPR provider will perform CPR compressions, using the two-thumbs technique, pressing down on the chest, keeping the anterior sensor between his thumbs and the victim's chest, so that the sensor moves up and down in fixed relation with the patient's chest, and keeping the posterior sensor between his fingers and the victim's spine, or at least keeping the posterior extending element between his fingers and the patient's back so that the posterior sensor moves up and down in fixed relation with the patient's back. The CPR provider will operate an associated control system, and energize the sensors, to analyze the sensor signals to determine chest compression depth, velocity of the compression monitor (including release velocity), and the rate of compression, compare the determined chest compression depth, release velocity and/or compression rate to the desired values, and operate an output device to provide prompts indicating whether the determined chest compression depth, release velocity and/or compression rate meets or fails to meet the desired values. The control system may also be operated to compare the measured depth of compression to a desired depth of compression and report to the CPR provider whether the achieved depth of compression meets or fails to meet the desired depth. Prior to the start of compressions, the CPR provider may optionally bring the anterior frame and posterior frame into contact with the body, and provide input to the control system that the anterior frame and posterior frame are in contact with the body.

The frame may be used to perform CPR compressions, including active compression/decompression, with or without the compression depth monitoring components of the system. The frame, with an adhesive surface on at least a portion of the interior surface of the anterior segment, can be installed about the thorax of a patient such that the adhesive secures the anterior segment to the patient's chest wall, over the sternum (that is, the preferred compression point). With the frame installed, CPR compressions are performed. Upon release of each compression, the resilient frame will resiliently expand toward its open configuration, thereby imparting some expansive force on the chest wall. If the patient is prone on a supportive surface, only the anterior segment need be adhesive. If the patient is held up, or prone on a soft surface, the posterior segment interior surface may be adhesive as well. This method may be used on adults and pediatrics as well as infants.

When used to provide CPR compressions with active compression/decompression the method entails providing the frame having an anterior segment and a posterior segment, and sized and dimensioned to fit at least partially around the thorax of the cardiac arrest victim with adhesive on a portion of the anterior segment is adhesive and, optionally, on the posterior segment, and installing the frame about the thorax of a cardiac arrest victim such that the adhesive secures the anterior segment to the cardiac arrest victim's chest wall. After installation, the CPR provider performs CPR chest compressions on the cardiac arrest victim, allowing the frame to expand between compressions to provide active decompression, with the resilience of the frame acting to restore the frame toward its relaxed opened position and thus exert upward pulling force on the thorax.

While the preferred embodiments of the devices and methods have been described in reference to the environment in which they were developed, they are merely illustrative of the principles of the inventions. Though illustrated for use with infants and the two-thumb compression technique, the devices may be used the two-finger technique, and the devices may sized and dimensioned for adult use, and used in otherwise standard CPR compressions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method for delivering cardiopulmonary resuscitation (CPR) chest compressions to a patient by a rescuer, the method comprising:
   positioning an anterior segment of one or more first layers of a resilient wrap-around structure comprising a first motion sensor on a sternum of the patient, the first motion sensor configured to generate a first motion signal, such that at least a portion of an interior surface of the anterior segment is adhered to the patient's chest;
   positioning a posterior segment of the one or more first layers of the resilient wrap-around structure comprising a second motion sensor on a back of the patient, the second motion sensor configured to generate a second motion signal;
   securing or releasing one or more additional layers of the resilient wrap-around structure to at least one of the one or more first layers of the resilient wrap-around structure to adjust a resilience of the resilient wrap-around structure, wherein the one or more additional layers are elongated along a length of the resilient wrap-around structure and are positioned between a tip of the anterior segment and a tip of the posterior segment;
   providing chest compressions to the patient such that the first motion sensor moves in fixed relation with the sternum of the patient and the second motion sensor moves in fixed relation with the back of the patient during the chest compressions;
   actively decompressing the chest by the resilient wrap-around structure after each chest compression to exert an expansive force on the patient's chest wall during a release phase of a chest compression cycle and to lift the patient's chest during the release phase, thereby hastening expansion and upward movement of the patient's chest relative to expansion from natural resilience of the patient's chest without the lift, wherein resilient expansion of the resilient wrap-around structure adhered to the patient's chest causes the expansive force to be exerted on the patient's chest wall, wherein the expansive force causes expansion and upward movement of the patient's chest and is exerted via the at least a portion of the interior surface of the anterior segment adhered to the patient's chest;
   receiving CPR related feedback, wherein the CPR related feedback is based at least in part on determined CPR chest compression parameters, wherein the chest compression parameters are determined based at least in part on the generated first motion signal and the generated second motion signal; and
   adjusting the CPR delivered to the patient based at least in part on the received CPR related feedback.

2. The method of claim 1, further comprising operating an associated control system, comprising a processor and a memory, configured to receive the first motion signal and the second motion signal.

3. The method of claim 2, wherein the associated control system is configured to calculate at least one of a depth of chest compression delivered by the rescuer or a release parameter indicative of active decompression.

4. The method of claim 3, wherein the associated control system provides feedback regarding the depth of chest compression or the release parameter indicative of active decompression.

5. The method of claim 4, further comprising modifying delivery of the chest compressions based upon the feedback.

6. The method of claim 4, wherein the feedback provides an indication to the rescuer to adjust one or more parameters of the chest compressions and/or release of the anterior segment during chest compressions.

7. The method of claim 6, wherein the one or more parameters include at least one of: a rate of the chest compressions, a depth of the chest compressions, and a release velocity of the chest compressions.

8. The method of claim 4, wherein the feedback includes a positive advisory in response to chest compressions that are adequate desired chest compression goals.

9. The method of claim 4, wherein the feedback includes a negative advisory in response to chest compressions that are inadequate or too excessive compared to desired chest compression goals.

10. The method of claim 9, wherein the desired chest compression goals are based on a determined size of the patient and include at least one of: a chest compression depth, a chest compression rate, and a release velocity.

11. The method of claim 4, wherein the feedback includes at least one of visual prompts, audio prompts, and haptic prompts.

12. The method of claim 2, further comprising inputting information related to a size of the patient into the associated control system.

13. The method of claim 2, wherein the associated control system determines a size of the patient in response to receiving an indication from the rescuer that the wrap-around structure is disposed about the patient.

14. The method of claim 1, further comprising selecting at least one of: an appropriate size of the wrap-around structure and a resilience at a point of use of the wrap-around structure.

15. The method of claim 1, further comprising adjusting the wrap-around structure in response to a determination of a size of the patient.

16. The method of claim 1, wherein providing chest compressions to the patient comprises holding the anterior segment and the posterior segment in fixed relation to the body of the patient by thumbs and fingers of the rescuer during the chest compressions.

17. The method of claim 1, wherein providing chest compressions to the patient comprises placing hands of the rescuer around a thorax of the patient such that thumbs of the rescuer are over the sternum of the patient and onto the anterior segment of a wrap-around structure and fingers of the rescuer are on the back of the patient and positioned on the posterior segment of the wrap-around structure.

18. The method of claim 1, wherein providing chest compressions to the patient includes squeezing a thorax of the patient with thumbs pressing on the sternum of the patient to push the sternum toward a spine.

19. The method of claim 1, wherein positioning the anterior segment and the posterior segment includes providing an input to the associated control system to indicate that the anterior segment and the posterior segment are in contact with the patient.

20. The method of claim 19, wherein the associated control system is a defibrillator that includes one or more input devices for receiving input from the rescuer.

21. The method of claim 20, wherein the one or more input devices include a keyboard, one or more soft-keys, and/or a touchscreen.

22. The method of claim 1, wherein the wrap-around structure is biased to an open configuration.

23. The method of claim 1, wherein the first motion sensor and second motion sensors are accelerometers that generate acceleration signals corresponding to acceleration of the chest and acceleration of the back of the patient during the chest compressions.

24. The method of claim 1, wherein the first motion sensor and second motion sensors are velocity sensors.

25. The method of claim 1, wherein the first motion sensor is a magnetic field sensor and the second motion sensor is a magnetic field generator.

26. The method of claim 1, comprising positioning of the anterior segment of the resilient wrap-around structure such that at least the portion of the interior surface of the anterior segment is secured to the patient's chest at least in part by the interior surface of the anterior segment being adhered to the patient's chest.

27. The method of claim 1, comprising positioning of the anterior segment of the resilient wrap-around structure such that at least the portion of the interior surface of the anterior segment is secured to the patient's chest at least in part by in part by the interior surface of the anterior segment being adhered to the patient's chest by an adhesive surface on the at least the portion of the interior surface of the anterior segment.

28. The method of claim 1, comprising receiving the CPR related feedback, wherein the determined CPR chest compression parameters comprise a depth and a rate of delivered chest compressions.

29. The method of claim 28, comprising receiving the CPR related feedback, wherein the CPR related feedback comprises display or audio output to be provided via an output device, and wherein the CPR related feedback provides an indication to the rescuer of the delivered chest compression depth and rate relative to a desired chest compression depth and rate.

30. The method of claim 1, comprising positioning the anterior segment, wherein a tip of the anterior segment comprises the interior surface of the anterior segment.

31. The method of claim 1, wherein positioning the anterior segment comprises positioning the first motion sensor on a tip of the anterior segment, and wherein positioning the posterior segment comprises positioning the second motion sensor on a tip of the posterior segment.

* * * * *